United States Patent
McDonald et al.

(10) Patent No.: US 10,126,247 B2
(45) Date of Patent: Nov. 13, 2018

(54) RUBBER CRUMB INSPECTION SYSTEM

(71) Applicant: Zeon Chemicals L.P., Louisville, KY (US)

(72) Inventors: David J. McDonald, Hattiesburg, MS (US); Mark Allen, Louisville, KY (US)

(73) Assignee: Zeon Chemicals L.P., Louisville, KY (US)

( * ) Notice: Subject to any disclaimer, the term of this patent is extended or adjusted under 35 U.S.C. 154(b) by 0 days.

(21) Appl. No.: 15/222,275

(22) Filed: Jul. 28, 2016

(65) Prior Publication Data

US 2017/0030838 A1    Feb. 2, 2017

Related U.S. Application Data

(60) Provisional application No. 62/198,719, filed on Jul. 30, 2015.

(51) Int. Cl.
*B07C 5/34* (2006.01)
*G01N 21/88* (2006.01)
(Continued)

(52) U.S. Cl.
CPC ....... *G01N 21/8806* (2013.01); *B07C 5/3422* (2013.01); *G01N 21/94* (2013.01);
(Continued)

(58) Field of Classification Search
CPC .................. B07C 5/342; B07C 5/3425; G01N 2021/8806; G01N 2021/8825; G01N 21/94
(Continued)

(56) References Cited

U.S. PATENT DOCUMENTS 5,409,119 A * 4/1995 Rao Datari ............... B07C 5/10
                                                          209/580
5,659,624 A * 8/1997 Fazzari ................. B07C 5/3422
                                                          209/580
(Continued)

FOREIGN PATENT DOCUMENTS

CN    102053091 A    5/2011
JP    H 03-113352 A   5/1991
(Continued)

OTHER PUBLICATIONS

Nichols, E., "Improving Product Quality in Rubber Manufacturing," ProSensus, Inc., 2016, downloaded on Aug. 8, 2016 from http://www.prosensus.com/multivariate-news/134-improving-product-quality-in-rubber-manufacturing, 2 pgs.

*Primary Examiner* — Joseph C Rodriguez
(74) *Attorney, Agent, or Firm* — Frost Brown Todd LLC

(57) ABSTRACT

An inspection system for inspecting rubber crumb includes a conveyor, lighting, a camera, and a controller. The conveyor is used to carry the rubber crumb. The lighting is positioned above the conveyor to illuminate the rubber crumb with at least 3,500 lumens. The camera is positioned adjacent to the lighting to take images of the illuminated rubber crumb in the lighted area. The controller receives the images from the camera and detects a contamination in the rubber crumb by determining whether there is a dark particle within the crumb. If a contamination is detected, it may be removed from the remaining rubber crumb.

10 Claims, 10 Drawing Sheets

(51) Int. Cl.
  *G01N 21/94* (2006.01)
  *B07C 5/342* (2006.01)
(52) U.S. Cl.
  CPC .............. *G01N 2201/0461* (2013.01); *G01N 2201/062* (2013.01)
(58) Field of Classification Search
  USPC ........................................ 209/576, 580, 581
  See application file for complete search history.

(56) References Cited

U.S. PATENT DOCUMENTS

| | | | |
|---|---|---|---|
| 5,927,620 A * | 7/1999 | Memon | B29B 17/02 241/17 |
| 6,011,620 A | 1/2000 | Sites et al. | |
| 6,260,495 B1 | 7/2001 | Stewart et al. | |
| 6,396,579 B1 | 5/2002 | Hayamizu et al. | |
| 6,532,064 B1 | 3/2003 | Hearn et al. | |
| 6,628,379 B1 | 9/2003 | Sudo et al. | |
| 7,227,148 B2 * | 6/2007 | Sato | A24B 1/04 250/339.11 |
| 7,298,870 B2 * | 11/2007 | Ikeda | B07C 5/3422 348/92 |
| 7,401,728 B2 | 7/2008 | Markham et al. | |
| 7,445,170 B2 * | 11/2008 | Cialone | B29B 17/02 241/24.17 |
| 7,660,440 B2 * | 2/2010 | Bourg, Jr. | G01N 21/8851 382/110 |
| 7,842,896 B1 * | 11/2010 | Calcoen | B07C 5/3427 209/576 |
| 7,968,814 B2 * | 6/2011 | Imai | B07C 5/3425 209/576 |
| 8,511,474 B2 * | 8/2013 | Maunder | B07B 9/00 209/12.2 |
| 9,101,962 B2 | 8/2015 | Ackley et al. | |
| 9,446,434 B2 * | 9/2016 | Hamid | B07C 5/3422 |
| 2004/0032979 A1 * | 2/2004 | Honda | G06T 7/0004 382/145 |
| 2006/0011134 A1 | 1/2006 | Wain et al. | |
| 2012/0165973 A1 * | 6/2012 | Earlam | B07C 5/00 700/223 |
| 2014/0366633 A1 | 12/2014 | Schroeder et al. | |

FOREIGN PATENT DOCUMENTS

| | | |
|---|---|---|
| JP | 2000346813 A | 12/2000 |
| KR | 10 07 84962 B1 | 12/2007 |

* cited by examiner

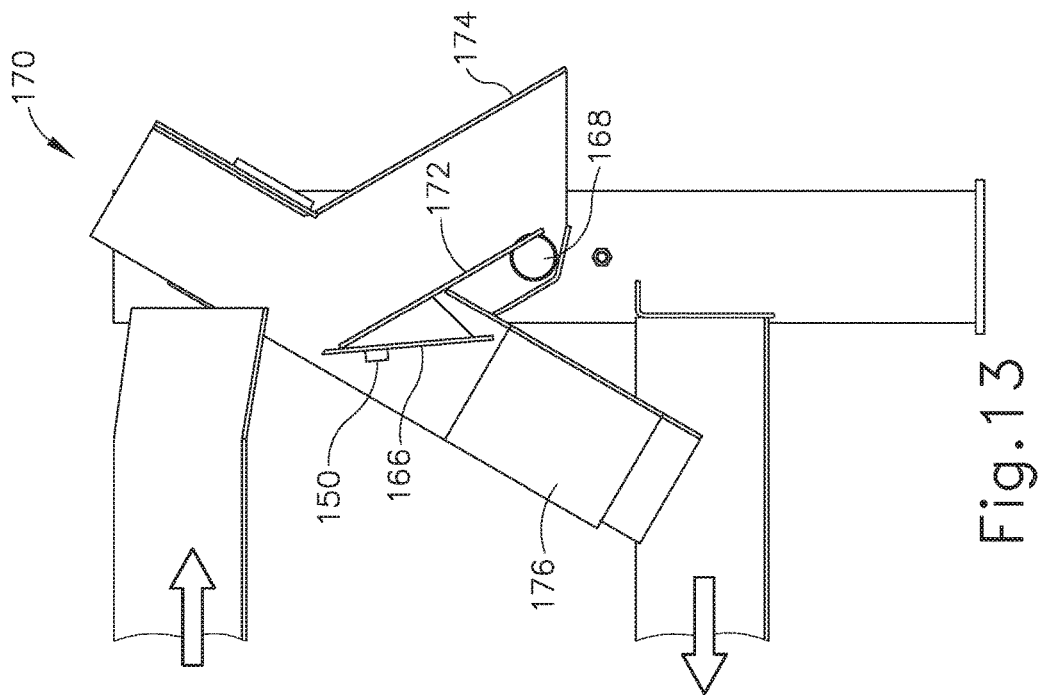
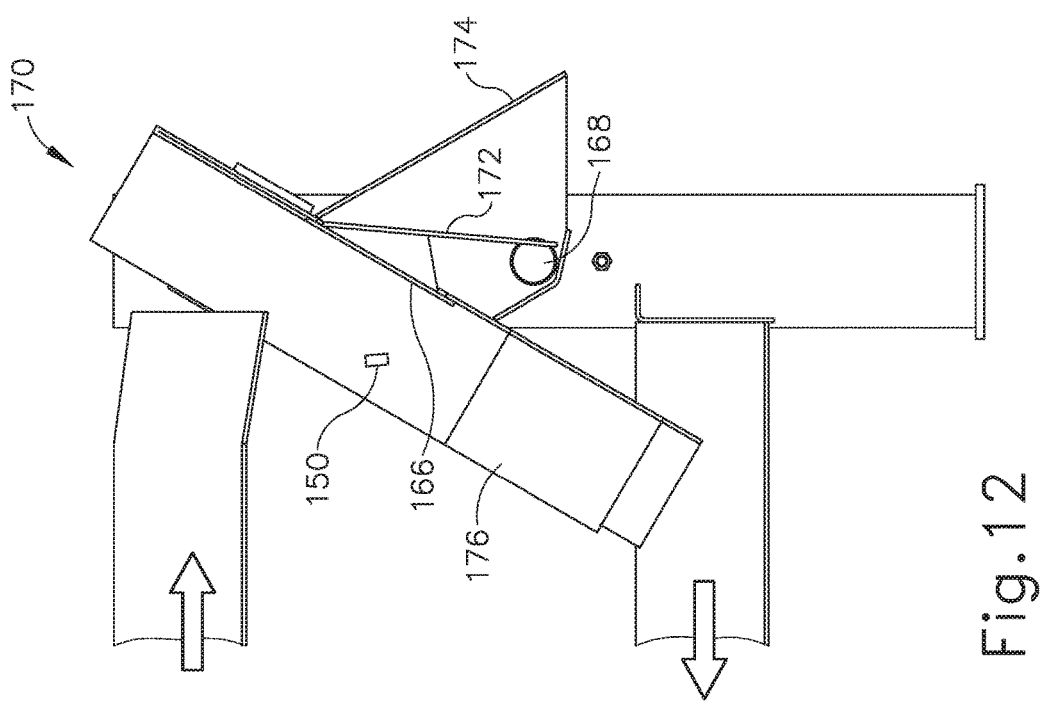

RUBBER CRUMB INSPECTION SYSTEM

PRIORITY

This application claims priority to U.S. Provisional Patent Application Ser. No. 62/198,719, entitled "Rubber Crumb Inspection System," filed on Jul. 30, 2015, the disclosure of which is incorporated by reference herein.

BACKGROUND

Rubber crumb is an intermittent form of an elastic polymer found during the manufacturing process of synthetic rubber. The crumb pieces are formed from either a latex suspension or polymer solution using a coagulation process. The rubber crumb may then be pressed into a block, or bale of rubber. Each bale may be about 25 kg to about 35 kg. The rubber bale may then be packaged for shipment to customers, which can include manufacturers of automotive parts, printer rollers, etc. Typically, the outer surfaces of the rubber bales are inspected by human or video inspection for appearance, including looking for contamination in the form of any material that contrasts to the routine color and tint of the finished product. Such contamination can lessen the utility of the rubber crumb and hence its value. Any contamination detected may be removed from the surface of the bale. However, because the rubber bales may not be translucent, these methods of inspection only view a limited amount of contents of each bale. For instance, less than about 5% of the contents of each bale may be inspected. It has further been found that contamination smaller than about 0.5 mm is difficult for technicians to detect visually. As such, there is a need for improved inspection system, such as inspecting the rubber crumb before it is pressed into a bale.

BRIEF DESCRIPTION OF THE DRAWINGS

While the specification concludes with claims which particularly point out and distinctly claim the invention, it is believed the present invention will be better understood from the following description of certain embodiments taken in conjunction with the accompanying drawings, in which like reference numerals identify the same elements.

FIG. 12 depicts a side view of a rejection system of the conveyor of FIG. 9 in a closed position.

FIG. 13 depicts the rejection system of FIG. 12 in an open position.

Figure 1:
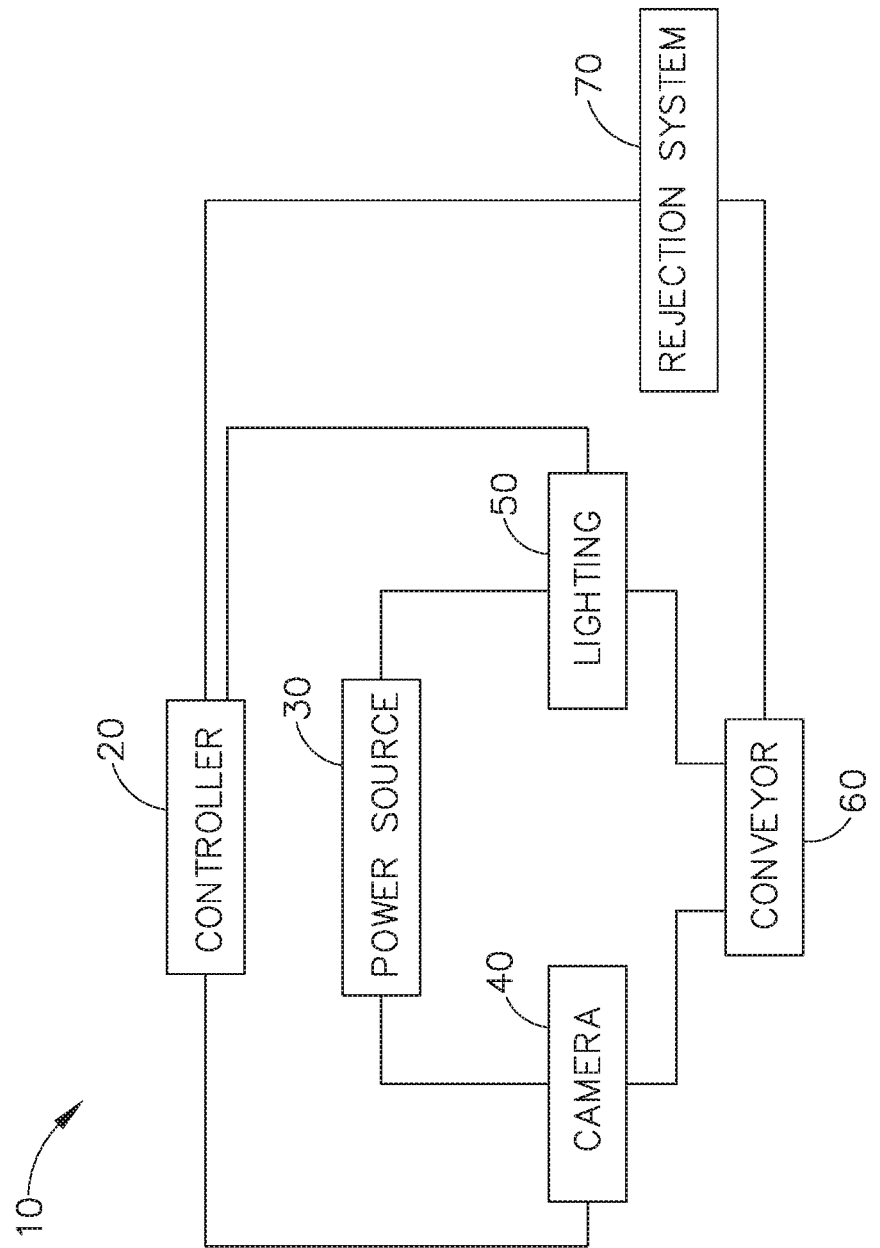
FIG. 1 depicts a schematic of an embodiment of a rubber crumb inspection system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain embodiments of the present disclosure should not be used to limit the scope of the present disclosure. Other examples, features, aspects, embodiments, and advantages of the invention will become apparent to those skilled in the art from the following description. As will be realized, various aspects of the present disclosure may take alternate forms, or have alternate or additional embodiments, without departing from the scope of the present disclosure. Accordingly, the drawings and descriptions should be regarded as illustrative in nature and not restrictive.

Rubber crumb can be formed by the polymerization reaction of monomers that can occur in either a solution of an organic solvent (e.g., toluene), or a latex (e.g, water-based) process. Once the polymer is formed, it can be coagulated or aggregated into small pieces called crumb. The rubber crumb can vary in diameter from about ¼ inch to about ¾ inch and has an irregular and inconsistent shape similar to popped corn. The color of the rubber crumb may vary between white to a light yellow or light brown. The coagulation process results in a slurry of crumb and water. The crumb may then be dried by squeezing and heating. When dry, the crumb may be weighed in a hopper and then pressed into a bale. The crumb may be inspected after it is coagulated and dried, but before it is packaged into a bale. This allows for the inspection of more of the contents of the rubber bale to produce a higher purity product. For instance, a contamination found in the rubber crumb, such as a black or dark piece, may be removed from the rubber crumb.

Figure 2:
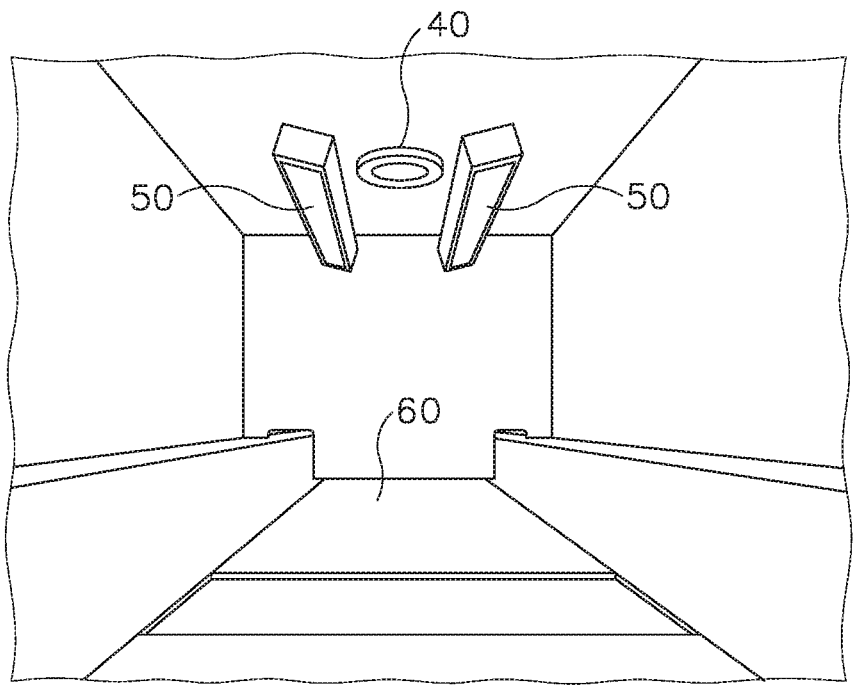
FIG. 2 depicts a perspective view of an embodiment of a lighting assembly for use with the rubber crumb inspection system of FIG. 1.
Figure 3:
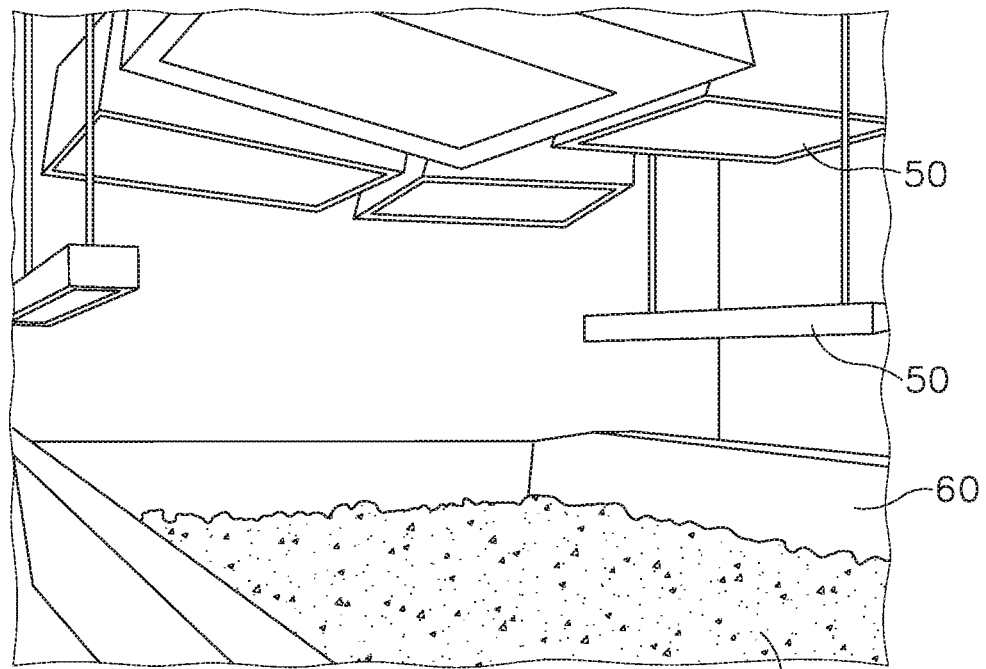
FIG. 3 depicts a perspective view of another embodiment of a lighting assembly for use with the rubber crumb inspection system of FIG. 1.

FIG. 1 shows an embodiment of an inspection system 10 that may be used to inspect the rubber crumb before it is packaged into a bale. The inspection system 10 comprises a controller 20 in communication with a camera 40 and lighting 50 such that the controller 20 is configured to operate both the camera 40 and the lighting 50. Alternatively, the camera 40 and the lighting 50 may each include a separate controller, or lighting 50 may not be operated by a controller. The camera 40 and lighting 50 are positioned over a conveyor 60 on which the rubber crumb 12 travels, as shown in FIGS. 2 and 3. A power source 30 is also in communication with the camera 40 and lighting 50 such that the power source 30 provides power to both the camera 40 and the lighting 50. Alternatively, the camera 40 and the lighting 50 may each include a separate power source. FIG.

1 shows the controller 20 coupled with the power source 30 such that the controller 20 may operate the power source 30. Alternatively, the power source 30 may not be coupled to a controller such that the power source 30 is manually powered on and off. The inspection system 10 of FIG. 1 further includes a rejection system 70 in communication with the conveyor 60 to remove any contamination found in the rubber crumb 12. For instance, the controller 20 may detect a black or dark piece of material in the rubber crumb 12 through the camera 40 and instruct the rejection system 70 to remove the black or dark piece from the remaining rubber crumb 12. This rejection system 70 may be operated by controller 20.

The conveyor 60 is configured to carry the rubber crumb 12 through the inspection system 10 such that the rubber crumb 12 is positioned substantially in a one-piece layer on the conveyor 60. The conveyor 60 may be a light color, such as white, to substantially match the color of the rubber crumb 12. For instance, the conveyor 60 may be coated in a white non-stick coating, such as the Tefzel ETFE low stick coating provided by DuPont. The speed of the conveyor 60 can vary between about 800 pounds per hour and about 6,000 pounds per hour. For instance, a speed of about 2,000 pounds per hour per foot of conveyor width is used to achieve a single crumb layer. As such, a maximum speed of about 3,000 pounds per hour is used for a conveyor 60 that is about 18 inches wide, and a maximum speed of about 6,000 pounds per hour is used for a conveyor 60 that is about 3 feet wide. If rates exceed these values, the rubber crumb 12 may pile on top of itself and not allow the camera 40 to inspect the entire rubber crumb 12. The width and/or the speed of the conveyor 60 may vary to achieve a single crumb layer.

The conveyor 60 may also vibrate to vibrate the rubber crumb 12 to thereby reveal a sufficient amount of the surface of each piece of rubber crumb 12 to the inspection system 10. For instance, the conveyor 60 may vibrate with an amplitude, or stroke, of between about 9/16 inch and about 1 inch and a frequency of between about 450 rpm and about 888 rpm. Of course other suitable configurations for the conveyor 60 will be apparent to one with ordinary skill in the art in view of the teachings herein.

The lighting 50 is positioned above the conveyor 60 to illuminate the rubber crumb 12 and reduce or eliminate shadows that may be caused by the inconsistent and irregular shape of the rubber crumb 12. Such shadows may be inadvertently detected by the controller 20 as a contamination. The lighting 50 is thereby used to enhance the contrast between any contamination and the rubber crumb 12. As best seen in FIG. 2, the lighting 50 may comprise a pair of LED linear light array bars, such as provided by Banner Engineering. In the illustrated embodiment, the bars are about 2 feet long and include a lumen rating of about 1760 lumens each, but other suitable configurations may be used. For instance, a minimum of about 3500 lumens may be used. The light emitted from the lighting 50 is configured as white light or daylight with a color temperature range of between about 5,000 K and 8,300 K. This may correspond to CIE daylight standards of D50-D75. The lighting 50 may be powered by about 24 VDC and about 4.2 A. As shown in FIG. 2, the lighting 50 is positioned substantially parallel with the conveyor 60, about 2 feet above a central portion of the conveyor 60, and aimed toward the edges of the pan of the conveyor 60. This illuminates the rubber crumb 12 at different angles under the camera 40 to minimize the occurrence of shadow false alarms, but the lighting 50 may be adjusted to other positions and angles. The lighting 50 may further include a shroud to reduce or eliminate any ambient lighting. Other suitable amounts and configurations for lighting 50 will be apparent to one with ordinary skill in the art in view of the teachings herein.

Figure 4:
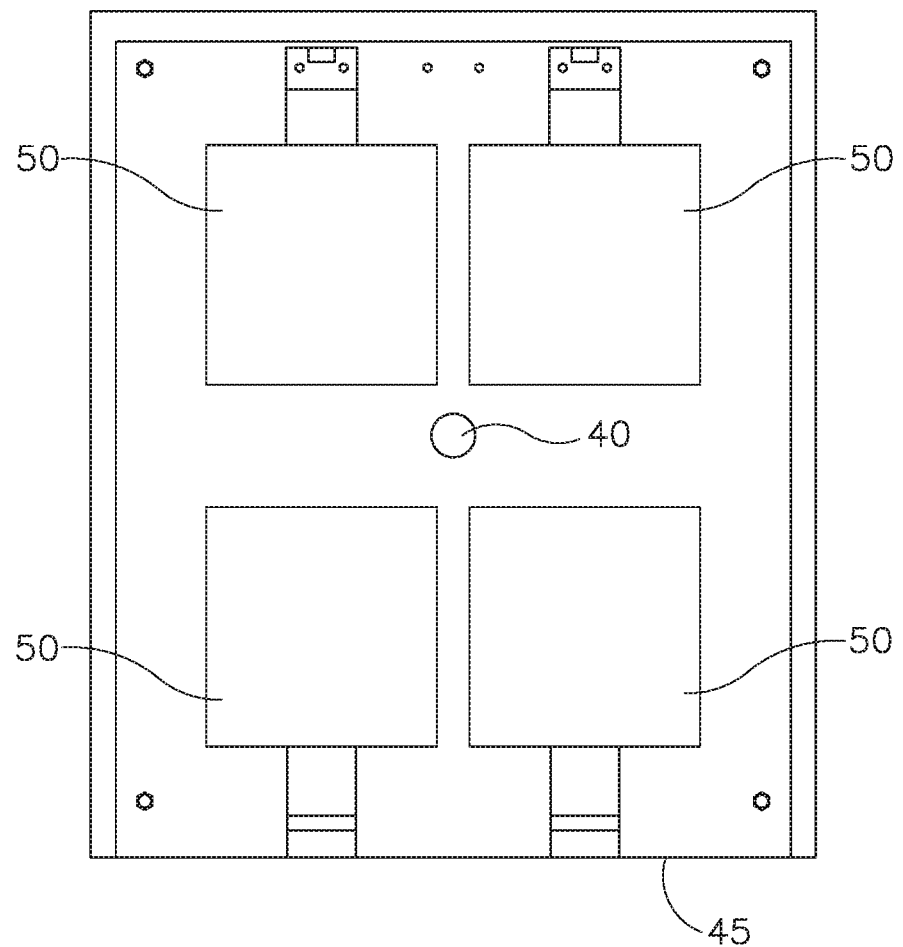
FIG. 4 depicts a top plan view of the lighting assembly of FIG. 3.

For instance, alternatively or additionally to the linear light array bars, LED box lights may be used, as shown in FIGS. 3 and 4. In the illustrated embodiment, four LED box lights are used, but any other suitable number of lights may be used. The box lights may include a lumen rating of about 15,000 lumens and have a power rating of about 141 W, but other suitable configurations may be used. The box lights may operate on 110 VAC. The box lights may be installed with light diffuser panels to distribute the light more evenly. As shown in FIG. 3, the light array bars may optionally be used with the box lights. In this embodiment, the linear array bars are positioned about 1 foot above each edge of the conveyor 60. While an LED light source is used in the present embodiment, other suitable light sources may be used (e.g., incandescent, halogen, fluorescent, etc.).

The camera 40 is then positioned substantially centrally between the lighting 50 above the conveyor 60. The camera 40 is configured to provide an examination area of a sufficient size for the controller 20. For instance, the camera 40 may include a camera viewing angle of between about 35 and 45 degrees, such as between about 40 and about 42 degrees, to provide an examination area with a width of between about 1.5 feet and about 3 feet and a length of between about 5 inches and about 11 inches. This examination area is lighted by lighting 50. The camera 40 may be positioned between about 2 feet and about 4 feet above the conveyor 60. The camera 40 may scan at a rate of between about 1.5 and about 4.5 frames per second. The scan rate may be adjusted depending on the quality of the controller 20. The shutter period for the camera 40 may be adjusted to regulate the amount of light entering the camera lens to allow enough light to minimize shadows without washing out the camera image. For instance, the shutter period can be between about 100 microseconds and about 1000 microseconds, such as between about 450 microseconds and about 975 microseconds. The camera 40 may be powered by about 12 VDC and about 1.2 A. The camera 40 may be JM Canty Camera Model No. VD4912-587. The camera 40 may be a color camera. Of course other suitable configurations for camera 40 will be apparent to one with ordinary skill in the art in view of the teachings herein.

Figure 5:
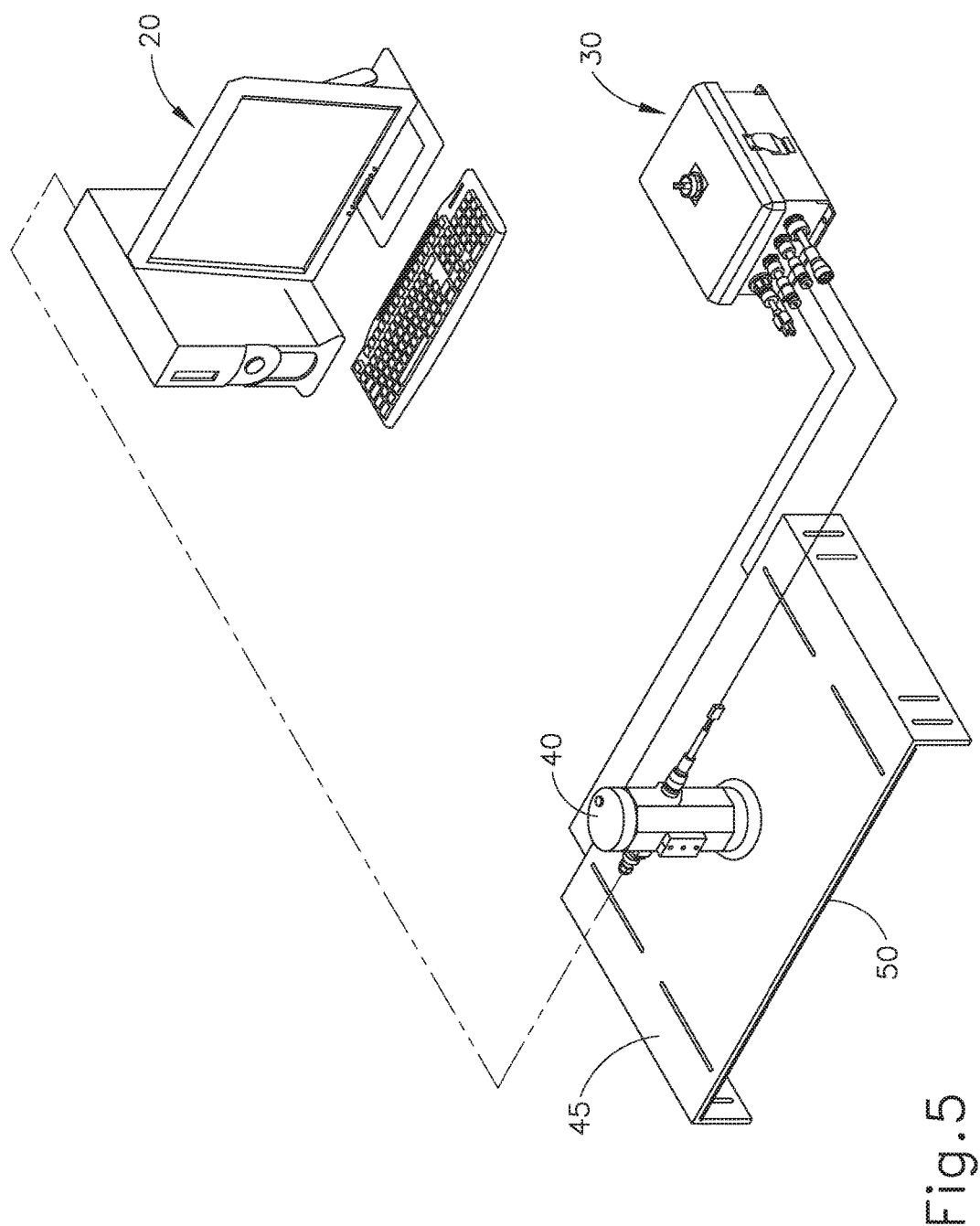
FIG. 5 depicts a perspective view of an embodiment of a controller, power source, camera, and lighting source for use with the rubber crumb inspection system of FIG. 1.

In some instances, the camera 40 and the lighting 50 may be mounted together using a mounting plate 45. FIG. 4 shows an embodiment of a mounting plate 45 for use with a camera 40 and a plurality of box lights, where the camera 40 is mounted centrally between the box lights. FIG. 5 shows another embodiment of a mounting plate 45 for use with a camera 40 and a pair of linear light arrays. The camera 40 is positioned through an opening within the mounting plate 45 substantially centrally between the lighting 50.

The controller 20, such as a computer, is then coupled with the camera 40, as shown in FIG. 5. For instance, the controller 20 may be in communication with the camera 40 via an Ethernet connection. The controller 20 receives the camera images from the camera 40. The controller 20 then detects any contamination by color contrast in the rubber crumb 12 in the camera images. For instance, the controller 20 detects a darker spot or particle (e.g., black, brown, tan, etc.) within the light colored rubber crumb 12. The controller 20 may detect one particle, down to a size of about 0.08 inches, within one frame signal. If a contamination is detected, the controller 20 signals the rejection system 70 to remove the contamination. Other suitable configurations for the controller 20 will be apparent to one with ordinary skill in the art in view of the teachings herein.

FIGS. 6-8C show an embodiment of a rejection system 70, comprising a gate 62 positioned within the conveyor 60 downstream of the camera 40. If the controller 20 detects a dark spot 14 (FIG. 8A) within the rubber crumb 12 on the conveyor 60, the controller 20 can signal the rejection system 70 to open the gate 62 (FIG. 8B) to remove the dark spot 14 from the remaining rubber crumb 12. The controller 20 can then signal the rejection system 70 to close the gate 62 (FIG. 8C) to continue inspecting the rubber crumb 12. For instance, when the dark spot 14 is detected, the controller 20 can wait between about 0.1 seconds and about 0.25 seconds until the dark spot 14 is positioned above the gate 62 of the rejection system 70 and turn off the conveyor 60. The controller 20 can then open the gate 62 for between about 1.75 seconds and about 2.5 seconds to allow the dark spot 14 to fall through the gate 62. The controller 20 can then close the gate 62 and restart the conveyor 60. The gate 62 may direct the dark spot 14 to a reject bin (not shown) when the gate 62 is opened.

Figure 6:
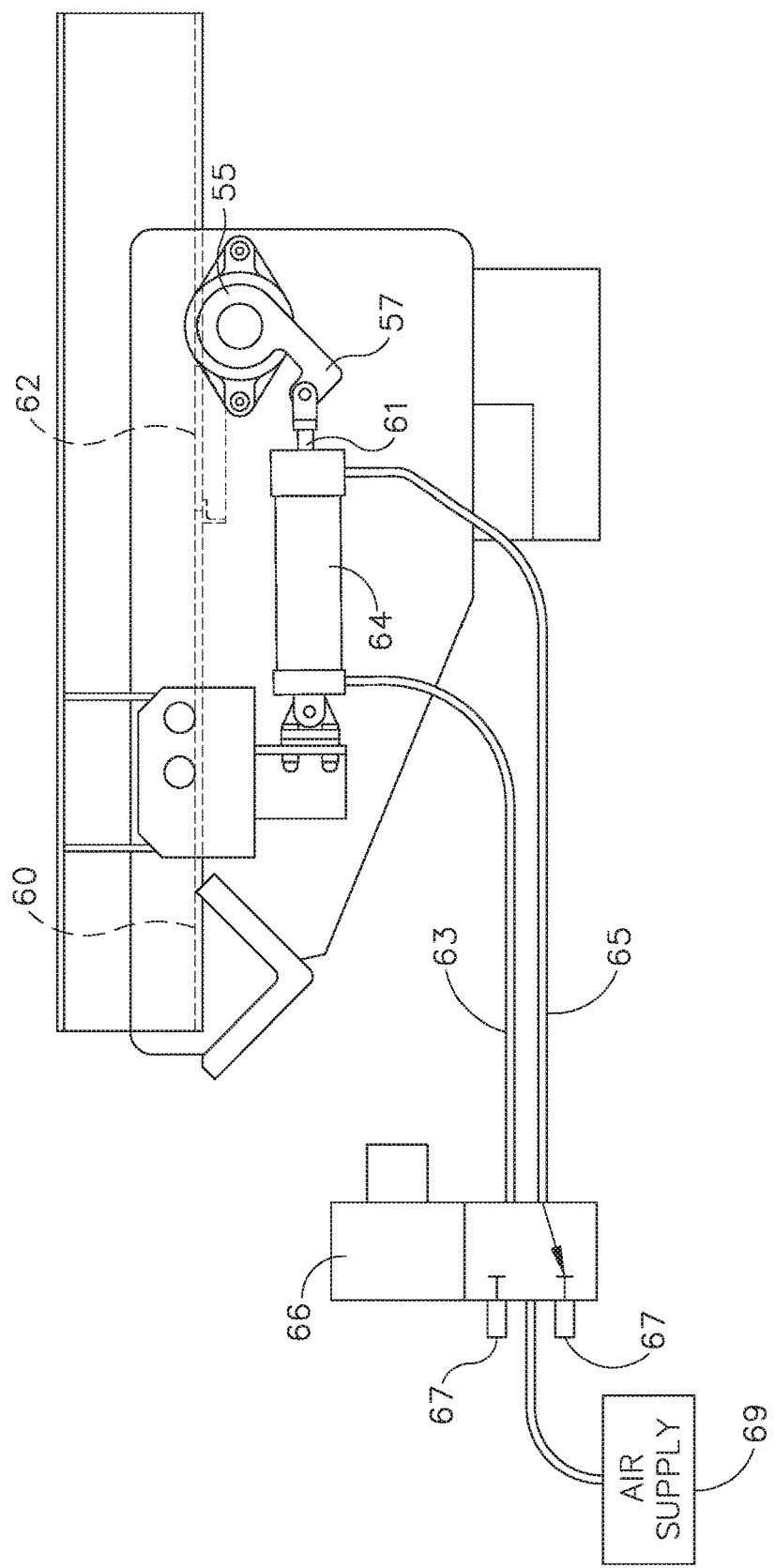
FIG. 6 depicts a side view of an embodiment of a rejection system for use with the rubber crumb inspection system of FIG. 1 in a closed position.
Figure 7:
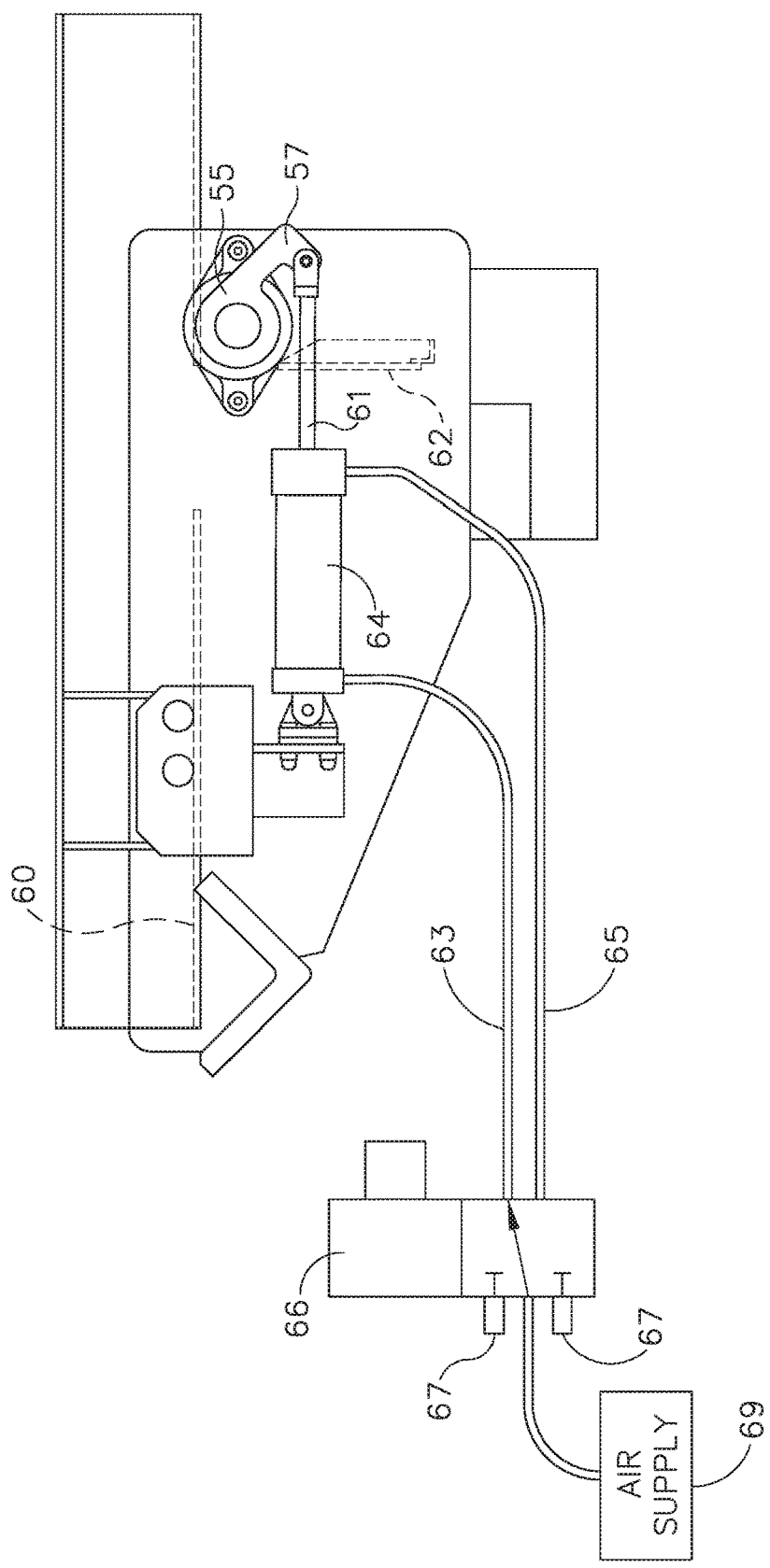
FIG. 7 depicts a side view of the rejection system of FIG. 6 in an open position.
Figure 8A:
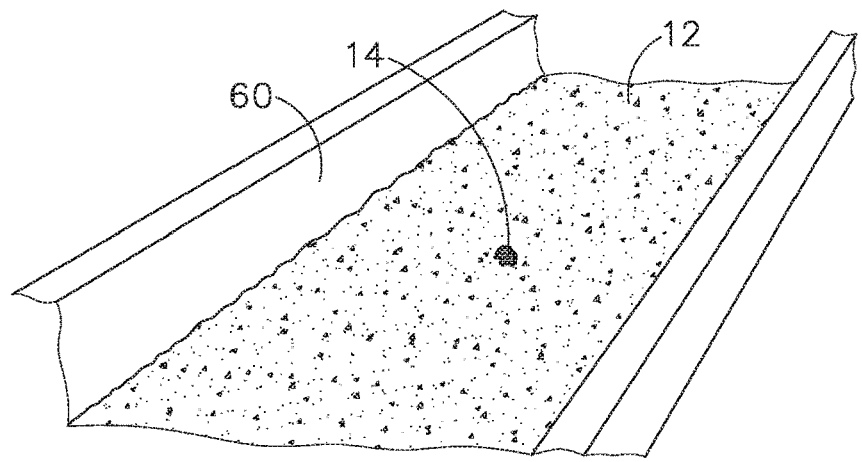
FIG. 8A depicts a perspective view of the rejection system of FIG. 6 in a closed position.
Figure 8B:
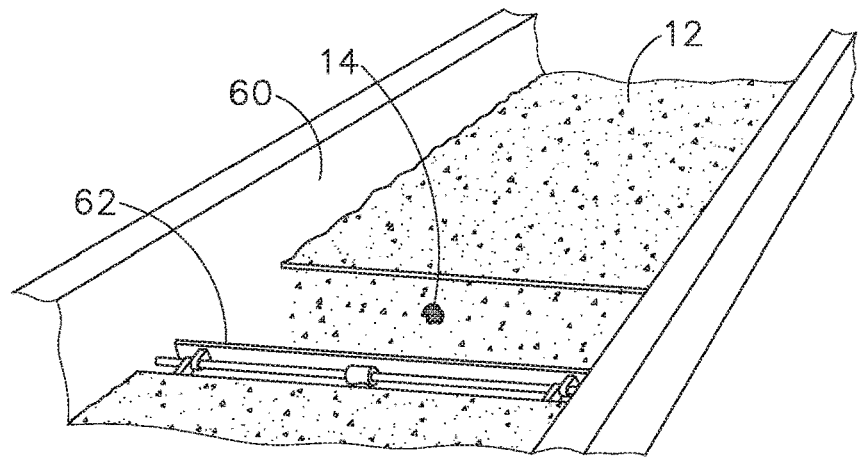
FIG. 8B depicts a perspective view of the rejection system of FIG. 6 in an open position.
Figure 8C:
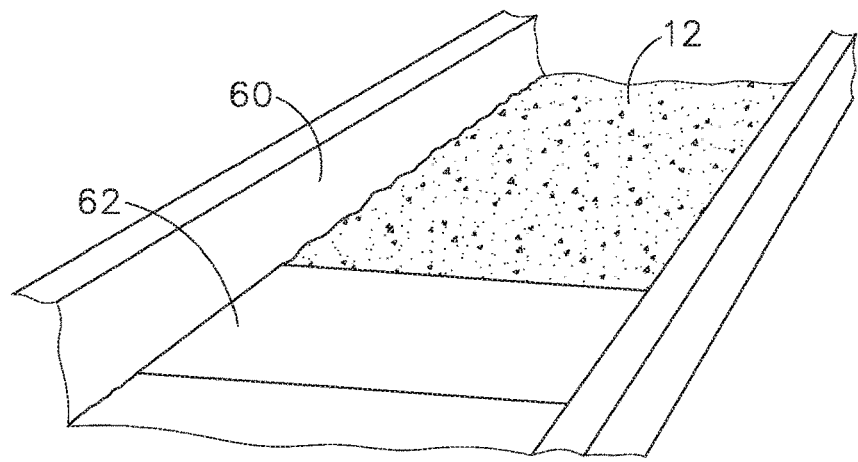
FIG. 8C depicts a perspective view of the rejection system of FIG. 6 returned to the closed position.

The gate 62 may be operated by a solenoid valve 66 and a pneumatic cylinder 64, as shown in FIGS. 6 and 7. For instance, the controller 20 may be in communication with the solenoid valve 66 to selectively open and close the valve 66. As shown in FIG. 6, the valve 66 is in communication with an air supply 69 to selectively supply air to the pneumatic cylinder 64. The valve 66 further comprises exhaust ports 67. The valve 66 is coupled with a port on the first end of the cylinder 64 via cable 63 and the valve 66 is coupled with another port on the second end of the cylinder 64 via cable 65. The cylinder 64 has an arm 61 positioned at the second end that selectively extends and retracts. The cylinder arm 61 is coupled with an arm 57 of a valve 55, which is coupled with the gate 62.

Accordingly, when the cylinder 64 is in a retracted position, as shown in FIG. 6, the gate 62 may be closed. The solenoid valve 66 may then be actuated to supply air from the air supply 69 to the first end of the pneumatic cylinder 64 through cable 63. The air thereby extends the arm 61 of the cylinder 64, which rotates the arm 57 of the valve 55 and the gate 62 to an open position, as shown in FIG. 7. The solenoid valve 66 may then be actuated to couple the second end of the pneumatic cylinder 64 with the exhaust port 67 through cable 65 and to decouple the air supply 69 to retract the arm 61 of the cylinder 64, as shown in FIG. 6. This rotates the arm 57 of the valve 55 and the gate 62 to a closed position. Alternatively, the cylinder 64 may close the gate 62 in the extended position and/or open the gate 62 in the retracted position. The cylinder 64 may also be operated by any other fluid. Other suitable configurations for operating the gate 62 will be apparent to one with ordinary skill in the art in view of the teachings herein.

Figure 9:
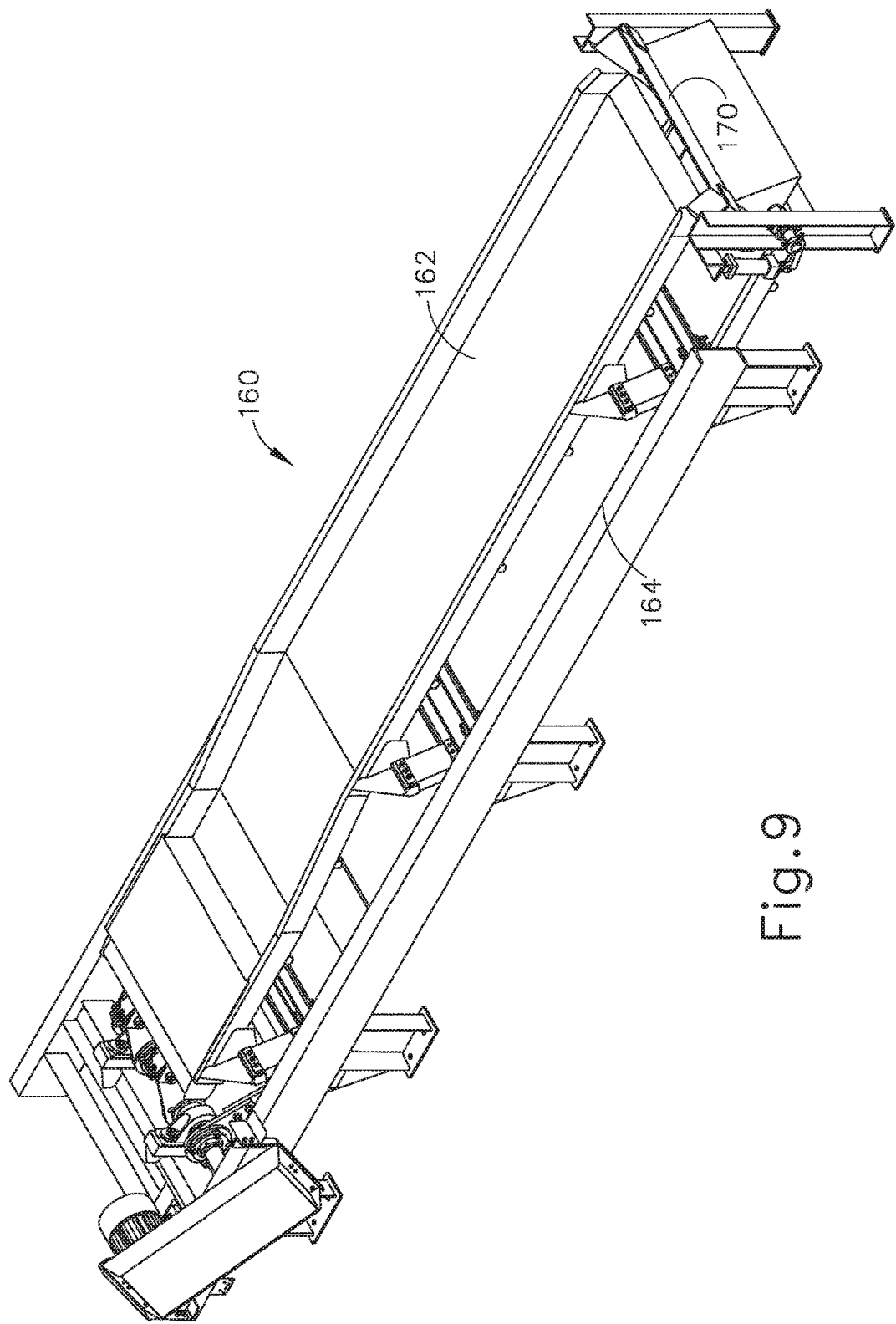
FIG. 9 depicts a perspective view of an embodiment of a conveyor for use with the rubber crumb inspection system of FIG. 1.
Figure 10:
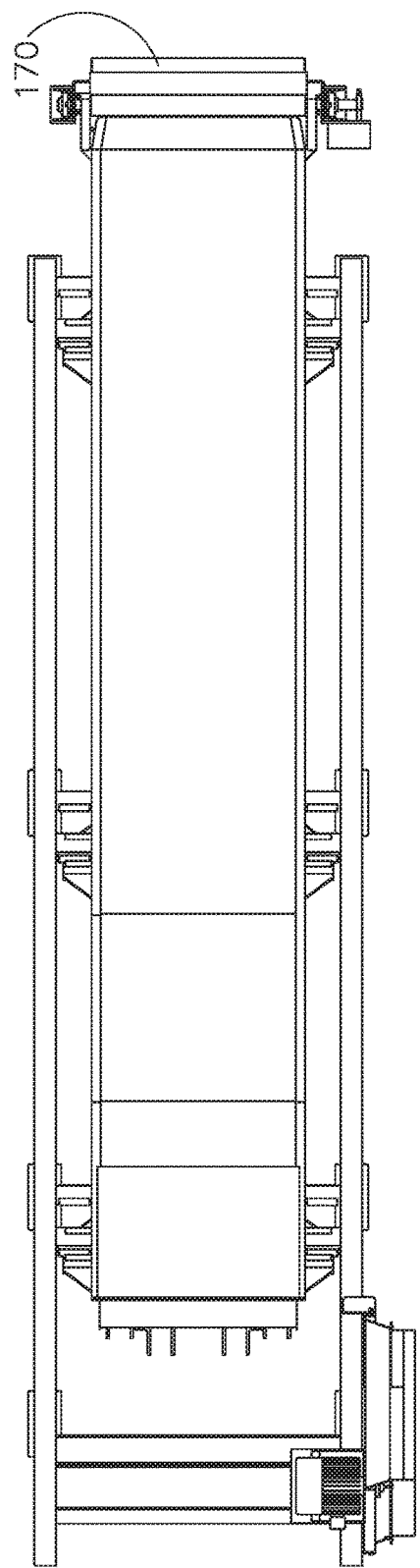
FIG. 10 depicts a top plan view of the conveyor of FIG. 9.
Figure 11:
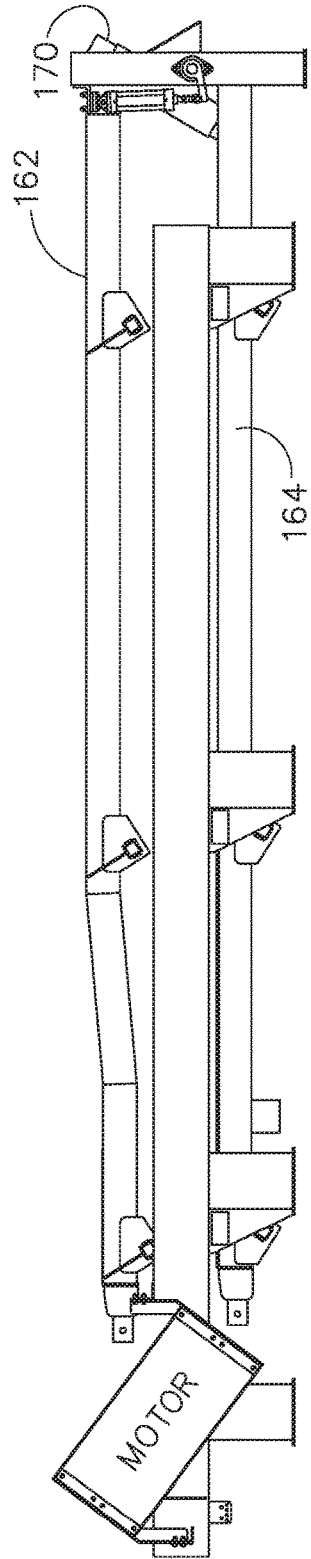
FIG. 11 depicts a side view of the conveyor of FIG. 9.

FIGS. 9-13 show another embodiment of a rejection system 170. For instance, FIG. 9 shows a conveyor 160 having a top conveyor 162 and a bottom conveyor 164 positioned underneath the top conveyor 162. This allows the rubber crumb 12 to travel along the top conveyor 162 toward the rejection system 170. If a contamination is not detected, the rejection system 170 remains in a closed position, as shown in FIG. 12, and allows the rubber crumb 12 to pass through a first chute 176 and onto the bottom conveyor 164, wherein the rubber crumb 12 continues to travel along the bottom conveyor 164 in an opposing direction. If a contamination is detected, the controller 20 opens a diverter 172 of the rejection system 170, as shown in FIG. 13, to direct the rubber crumb 12 from the top conveyor 162 to a second chute 174. For instance, the diverter 172 is coupled with a valve 168 that is configured to selectively rotate the diverter 172. When the diverter 172 is rotated to the open position, the diverter 172 pushes a gate 166 to an open position to abut against a stopper 150. The diverter 172 and the gate 166 thereby close the first chute 176 to direct the rubber crumb 12 to the second chute 174. The second chute 174 may lead to a reject bin (not shown). The diverter 172 of the rejection system 170 may also be operated by a solenoid valve and pneumatic cylinder, similar to the gate 62 described above.

It should be understood that any one or more of the teachings, expressions, embodiments, examples, etc. disclosed herein may be combined with any one or more of the other teachings, expressions, embodiments, examples, etc. that are disclosed herein. The teachings, expressions, embodiments, examples, etc. disclosed herein should therefore not be viewed in isolation relative to each other. Various suitable ways in which numerous aspects of the present disclosure may be combined will be readily apparent to those of ordinary skill in the art in view of the teachings disclosed herein. Such modifications and variations are intended to be included within the scope of both the present disclosure and the claims.

Other suitable rejection systems 70, 170 may be used. For instance, if a contamination is detected, the contamination may be picked out of the remaining rubber crumb 12 or an arm may sweep across the conveyor 60, 160 to remove the contamination. Alternatively or additionally, the contamination may be manually removed from the rubber crumb 12. The conveyor 60, 160 may be stopped while the contamination is removed, or the conveyor 60, 160 may continue to move. If the rubber crumb 12 is sent to a reject bin to remove the contamination, the contaminated particles may be sorted from the rest of the rubber crumb 12 in the reject bin and the sorted rubber crumb 12 may be returned to the conveyor 60, 160.

Having shown and described various embodiments of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, examples, embodiments, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

What is claimed is:

1. An inspection system for inspecting rubber crumb comprising:
   (a) a conveyor configured to carry the rubber crumb;
   (b) lighting positioned above the conveyor such that the lighting is configured to illuminate the rubber crumb with at least 3,500 lumens;
   (c) a camera positioned above the conveyor adjacent to the lighting, wherein the camera is configured to take images of the rubber crumb in the lighted area; and
   (d) a controller in communication with the camera such that the controller is configured to receive the images from the camera, wherein the controller is configured to detect a contamination within the rubber crumb by detecting a contamination particle that is darker than the rubber crumb and the conveyor.

2. The inspection system of claim 1 further comprising a rejection system in communication with the controller, wherein the rejection system is configured to remove the contamination when the contamination is detected by the controller.

3. The inspection system of claim 2, wherein the rejection system comprises a gate aligned with the conveyor that is selectively opened by the controller.

4. The inspection system of claim 2, wherein the rejection system comprises a diverter selectively operable by the controller to divert the contamination away from the conveyor.

5. The inspection system of claim 1, wherein the lighting is positioned centrally above the conveyor and pointed toward each edge of the conveyor.

6. The inspection system of claim 1, wherein the conveyor comprises a speed of about 2,000 pounds per hour per foot of the width of the conveyor.

7. The inspection system of claim 1, wherein the camera comprises a frame rate of between about 1.5 and about 4.5 frames per second.

8. The inspection system of claim 1, wherein the camera comprises a shutter period of between about 100 microseconds and about 1000 microseconds.

9. The inspection system of claim 1, wherein the contamination comprises a diameter greater than or equal to about 0.08 inches.

10. The inspection system of claim 1, wherein the lighting comprises a color temperature range between about 5,000K and about 8,300K.

* * * * *